United States Patent
Lee et al.

(10) Patent No.: US 10,765,322 B2
(45) Date of Patent: Sep. 8, 2020

(54) FAST PARALLEL OPTICAL COHERENCE TOMOGRAPHIC IMAGE GENERATING APPARATUS AND METHOD

(71) Applicant: KOREA BASIC SCIENCE INSTITUTE, Daejeon (KR)

(72) Inventors: Kye Sung Lee, Daejeon (KR); Ki Soo Chang, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 16 days.

(21) Appl. No.: 16/164,543

(22) Filed: Oct. 18, 2018

(65) Prior Publication Data

US 2019/0117077 A1 Apr. 25, 2019

(30) Foreign Application Priority Data

Oct. 19, 2017 (KR) .......................... 10-2017-0136014

(51) Int. Cl.
*A61B 5/00* (2006.01)
*G01B 9/02* (2006.01)
(Continued)

(52) U.S. Cl.
CPC .............. *A61B 5/0066* (2013.01); *A61B 3/00* (2013.01); *G01B 9/02034* (2013.01);
(Continued)

(58) Field of Classification Search
CPC .. A61B 5/0066; A61B 3/102; G01L 39/02091
See application file for complete search history.

(56) References Cited

U.S. PATENT DOCUMENTS 9,310,186 B2   4/2016  Abdulhalim et al.
2008/0013960 A1* 1/2008  Tearney ............... A61B 5/0062
                                            398/139
(Continued)

FOREIGN PATENT DOCUMENTS

JP      2013068636 A     4/2013
KR  1020150120891 A    10/2015
(Continued)

OTHER PUBLICATIONS

Bonin et al., "In vivo Fourier-domain full-field OCT of the human retina with 1.5 million A-lines/s," Optics Letters, vol. 35, No. 20, Oct. 15, 2010, pp. 3432-3434.
(Continued)

*Primary Examiner* — Michael P LaPage
(74) *Attorney, Agent, or Firm* — Quarles & Brady LLP (57) ABSTRACT

Provided is a fast parallel optical coherence tomographic image generating method including dispersing light into N spectral regions $\Delta\lambda_1$ through $\Delta\lambda_N$ sequentially from a low frequency wavelength to a high frequency wavelength, the light being emitted from a broadband light source of a fast parallel optical coherence tomographic image generating apparatus, N being an integer greater than or equal to 2, splitting the light emitted from the broadband light source to be incident on a sample and a reference mirror, partitioning the sample into N image regions $P_1$ through $P_N$, discretely controlling a beam scanner such that the light emitted from the broadband light source is incident on the sample at a position changed by a preset distance, acquiring an interference spectral image through interference light formed in response to interference of measurement light and reference light, and generating a tomographic image of the sample using the interference spectral image.

9 Claims, 9 Drawing Sheets

(51) Int. Cl.
*A61B 3/00* (2006.01)
*A61B 3/10* (2006.01)

(52) U.S. Cl.
CPC ..... *G01B 9/02044* (2013.01); *G01B 9/02083* (2013.01); *G01B 9/02091* (2013.01); *A61B 3/102* (2013.01)

(56) References Cited

U.S. PATENT DOCUMENTS

| | | | | |
|---|---|---|---|---|
| 2008/0094637 | A1* | 4/2008 | de Boer | A61B 5/0059 356/479 |
| 2008/0097225 | A1* | 4/2008 | Tearney | A61B 5/0075 600/478 |
| 2015/0374246 | A1 | 12/2015 | Yelin et al. | |
| 2018/0356344 | A1* | 12/2018 | Yi | G02B 21/002 |
| 2019/0223729 | A1* | 7/2019 | Frisken | G01B 9/02091 |

FOREIGN PATENT DOCUMENTS

| | | |
|---|---|---|
| KR | 101601899 B1 | 3/2016 |
| KR | 1020160125041 A | 10/2016 |
| KR | 101716372 B1 | 3/2017 |
| KR | 101746353 B1 | 6/2017 |

OTHER PUBLICATIONS

Fechtig et al., "Line-field parallel swept source interferometric imaging at up to 1 MHz," Optics Letters, vol. 39, No. 18, Sep. 15, 2014, pp. 5333-5336.

Liu et al., "Spectrally encoded extended source optical coherence tomography," Optics Letters, vol. 39, No. 24, Dec. 15, 2014, pp. 6803-6806.

* cited by examiner

In vivo human fingertip imaging at 212 kHz

FIG. 7A

Whole body leaf image at 425 kHz

FIG. 7B

FAST PARALLEL OPTICAL COHERENCE TOMOGRAPHIC IMAGE GENERATING APPARATUS AND METHOD

CROSS-REFERENCE TO RELATED APPLICATION(S)

This application claims the priority benefit of Korean Patent Application No. 10-2017-0136014 filed on Oct. 19, 2017, in the Korean Intellectual Property Office, the disclosure of which is incorporated herein by reference for all purposes.

BACKGROUND

1. Field

One or more example embodiments relate to a fast parallel optical coherence tomographic image generating apparatus and method.

2. Description of Related Art

In a medical environment, optical coherence tomography (OCT) has been used to acquire a tomographic image of a measurement target. OCT is a technique that acquires a high-resolution tomographic image by radiating an infrared ray on the measurement target and analyzing a difference in time of arrival and amount of light reflected according to a property of a tissue using an optical interferometer.

OCT is excellent at imaging depth and speed when compared to a confocal reflecting microscope and has a relatively high resolution when compared to ultrasonic imaging and thus, is widely used to acquire three-dimensional (3D) structure images of the eyes, the skin, and the heart and blood vessels.

Currently, in the field of bio and medical optical coherence imaging, there is a need to develop a system capable of fast imaging while maintaining a high image contrast to continuously perform in-vivo imaging in a short period.

However, a wavelength division system using a currently commercialized spectrometer has a difficulty in increasing an imaging speed, due to a speed of a camera.

The above description has been possessed or acquired by the inventor(s) in the course of conceiving the present invention and is not necessarily an art publicly known before the present application is filed.

SUMMARY

An aspect provides a fast parallel optical coherence tomographic image generating apparatus and method.

According to an aspect, there is provided a fast parallel optical coherence tomographic image generating method including dispersing light into N spectral regions $\Delta\lambda_1$ through $\Delta\lambda_N$ sequentially from a low wavelength to a high wavelength, the light being emitted from a broadband light source of a fast parallel optical coherence tomographic image generating apparatus, N being an integer greater than or equal to "2", splitting the light emitted from the broadband light source to be incident on a sample and a reference mirror, partitioning the sample into N image regions $P_1$ through $P_N$, discretely controlling a beam scanner such that the light emitted from the broadband light source may be incident on the sample at a position changed by a preset distance, acquiring an interference spectral image through interference light formed in response to interference of measurement light and reference light, the measurement light being light corresponding to at least two of the N spectral regions and being reflected from the sample and the reference light being light corresponding to the at least two spectral regions and being reflected from the reference mirror, and generating a tomographic image of the sample using the interference spectral image.

The N spectral regions may be incident on the sample at the same spectral distance which is a physical width, and a distance between the N image regions of the sample may be equal to the spectral distance.

The preset distance may be expressed by a product of the spectral distance and a number of image regions to be skipped by an end portion of the light radiated on the sample for each step among the N image regions.

In the discretely controlling, an overall distance the light is to be moved through the beam scanner along a single line may be calculated by the following equation, $$D = 2(N \times w) - 2(n \times w) \qquad \text{<Equation>}$$

(Here, D denotes the overall distance, N denotes a number of the image regions, n denotes the number of image regions to be skipped by the end portion of the light radiated on the sample for each step, and w denotes the spectral distance).

The discretely controlling may include determining whether a distance the radiated light is moved through the beam scanner is greater than the overall distance, moving the radiated light to an initial position of a subsequent line, if the distance the radiated light is moved is greater than the overall distance, and moving the radiated light the preset distance, if the distance the radiated light is moved is less than the overall distance.

The generating may include dividing the interference spectral image into N regions by wavelength and inputting the N regions into respective pixels of a line scan camera.

A number of the pixels of the line scan camera may be greater than or equal to "N", and the N regions into which the interference spectral image is divided may be incident on the respective pixels of the line scan camera.

The fast parallel optical coherence tomographic image generating apparatus may include an object lens configured to receive light reflected from the beam scanner, and have a common optical path from the broadband light source to the object lens.

The fast parallel optical coherence tomographic image generating apparatus may further include a split window disposed between the object lens and the sample, the split window including a beam splitter configured to reflect light incident from the object lens toward the reference mirror.

The fast parallel optical coherence tomographic image generating apparatus may further include a first compensation window disposed between the split window and the reference mirror, the first compensation window having a greater thickness than the split window so as to compensate for a difference in optical path of the reference light.

The fast parallel optical coherence tomographic image generating apparatus may further include a cover glass positioned between the split window and the sample, and a second compensation window disposed between the first compensation window and the reference mirror, the second compensation window and the cover glass having the same thickness so as to compensate for a difference in optical path of the reference light.

The fast parallel optical coherence tomographic image generating apparatus may further include a cube-type split window disposed between the object lens and the sample, the to cube-type split window including a beam splitter configured to reflect light incident from the object lens toward the reference mirror, the cube-type split window having a symmetrical shape with respect to the beam splitter.

According to another aspect, there is provided a fast parallel optical coherence tomographic image generating apparatus including a broadband light source configured to emit high-power light, a probe configured to receive the light from the broadband light source, illuminate a sample with the received light, and interfere with light reflected from the sample, a spectrometer configured to receive the interfered light from the probe, analyze a wavelength of the interfered light, and generate an interference spectral image of the interfered light, and a controller configured to generate a tomographic image of the sample through the interference spectral image generated by the spectrometer, wherein the probe may include a first dispersive element configured to disperse the light entering the probe from the broadband light source by wavelength, a beam scanner configured to reflect light passing through the first dispersive element toward the sample and adjust a position at which the light is radiated on the sample, an object lens configured to refract the light reflected by the beam scanner toward the sample, and an interferer configured to radiate a portion of the light output from the object lens to the sample, radiate a remaining portion of the light to a reference mirror, and generate interference light by synthesizing light reflected from the sample and light reflected from the reference mirror, wherein the spectrometer may include a second dispersive element configured to disperse interference light incident from the probe to the spectrometer by wavelength, and a line camera configured to analyze a wavelength of light passing through the second dispersive element and generate the interference spectral image, wherein the controller may be configured to discretely control the beam scanner such that the light emitted from the broadband light source may be incident on the sample at a position changed by a preset distance.

The line camera may include an image sensor including a plurality of pixels arranged in a line, and the light dispersed through the second dispersive element by wavelength may be input into each of the pixels of the line camera by wavelength.

A range of wavelength for each region into which the light is dispersed by the second dispersive element may be the same as a range of wavelength for each region into which the light is dispersed by the first dispersive element.

According to still another aspect, there is provided a fast parallel optical coherence tomographic image generating apparatus including a broadband light source configured to emit high-power light, a probe configured to receive the light from the broadband light source, illuminate a sample with the received light, and interfere with light reflected from the sample, a spectrometer configured to receive the interfered light from the probe, analyze a wavelength of the interfered light, and generate an interference spectral image of the interfered light, and a controller configured to generate a tomographic image of the sample through the interference spectral image generated by the spectrometer, wherein the probe may include a first dispersive element configured to disperse the light entering the probe from the broadband light source by wavelength, a beam scanner configured to reflect light passing through the first dispersive element toward the sample and adjust a position at which the light is radiated on the sample, an object lens configured to refract the light reflected by the beam scanner toward the sample, and an interferer configured to radiate a portion of the light incident to the probe to the sample through the first dispersive element, radiate a remaining portion of the light to a reference mirror, and generate interference light by synthesizing light reflected from the sample and light reflected from the reference mirror, wherein the spectrometer may include a second dispersive element configured to disperse interference light incident from the probe to the spectrometer by wavelength, and a line camera configured to analyze a wavelength of light passing through the second dispersive element and generate the interference spectral image, wherein the controller may be configured to discretely control the beam scanner such that the light emitted from the broadband light source may be incident on the sample at a position changed by a preset distance.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 1:
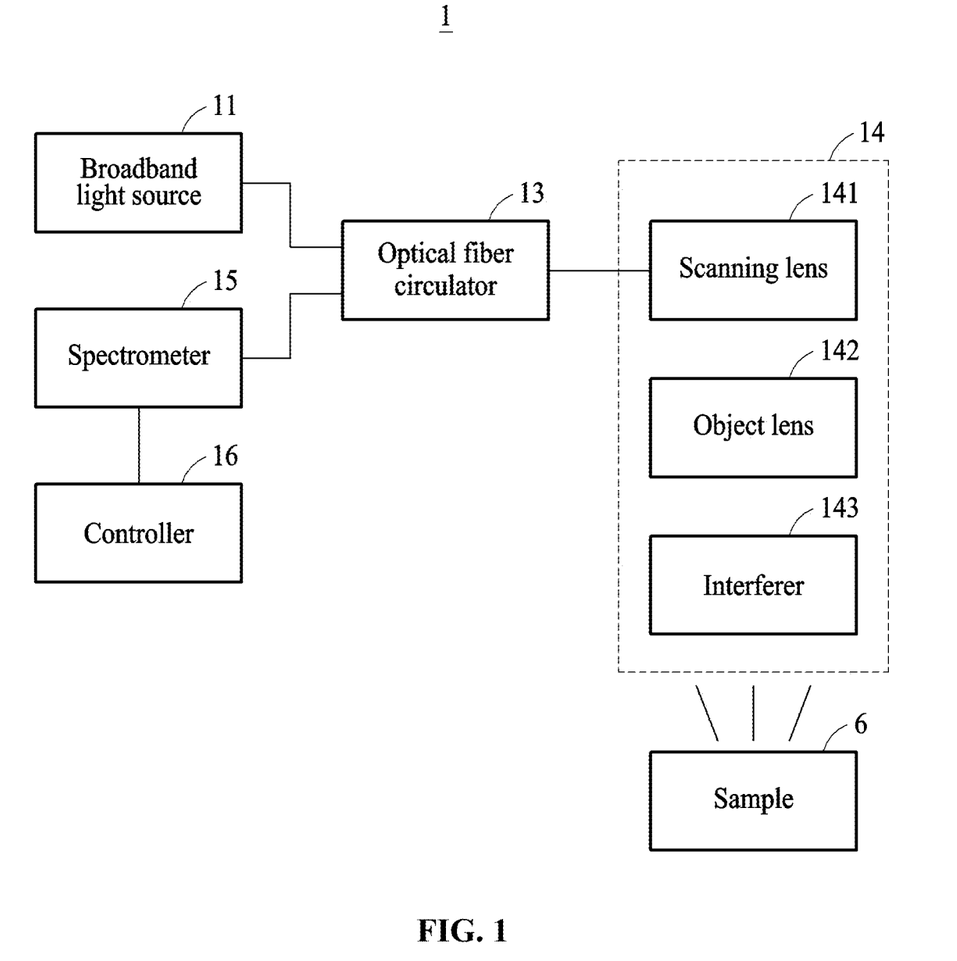
FIG. 1 is a block diagram illustrating a fast parallel optical coherence tomographic image generating apparatus according to an example embodiment.
Figure 2A:
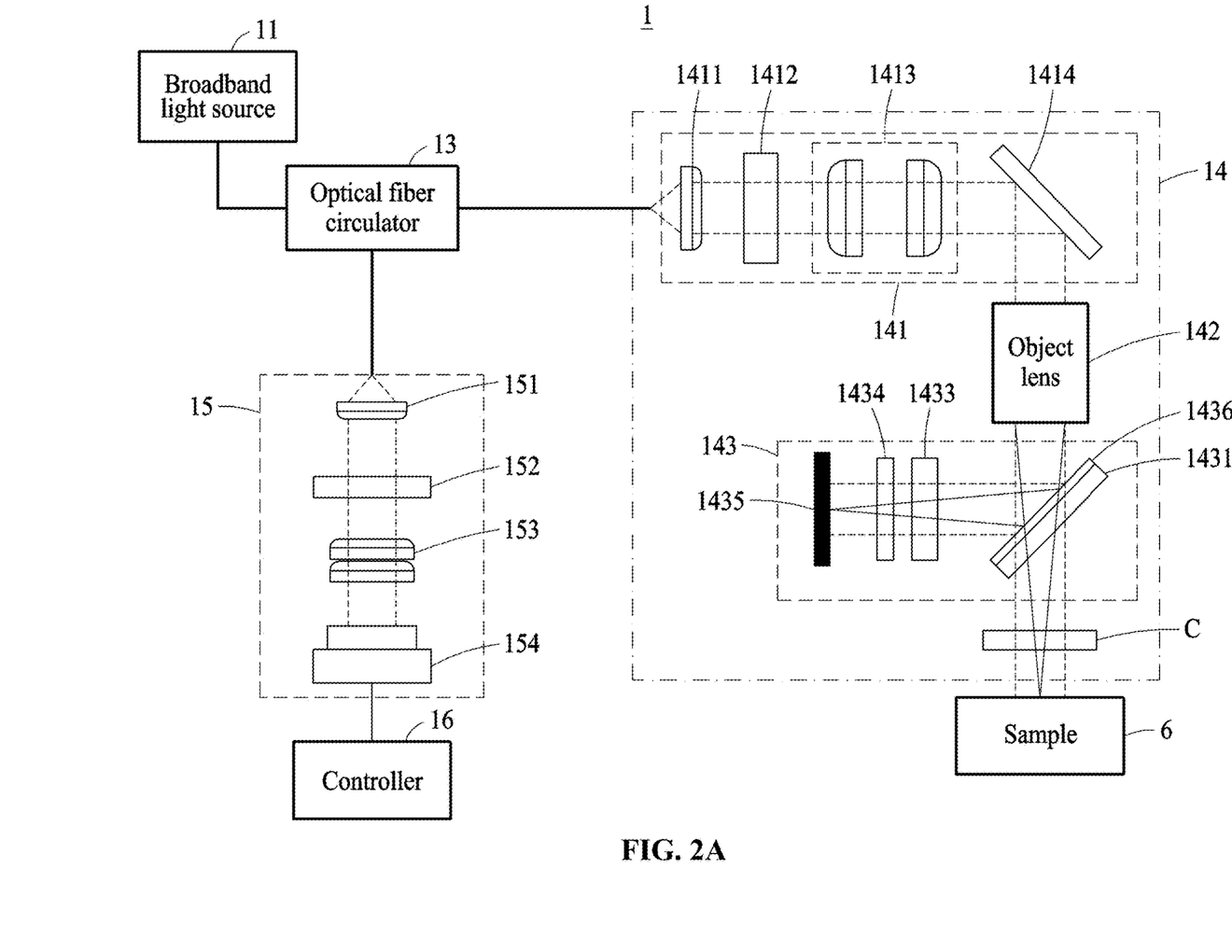
FIG. 2A is a block diagram illustrating a fast parallel optical coherence tomographic image generating apparatus according to an example embodiment.

FIG. 1 is a block diagram illustrating a fast parallel optical coherence tomographic image generating apparatus according to an example embodiment, and FIG. 2A is a block diagram illustrating the fast parallel optical coherence tomographic image generating apparatus according to an example embodiment.

Referring to FIGS. 1 and 2A, a fast parallel optical coherence tomographic image generating apparatus 1 may acquire a tomographic image of a sample 6 by performing spectrally encoded and parallel optical coherence tomography (OCT). For example, the fast parallel optical coherence tomographic image generating apparatus 1 may include a broadband light source 11, an optical fiber circulator 13, a probe 14, a spectrometer 15, and a controller 16.

The broadband light source 11 may output a low-coherence light having a wide dispersive radiation spectrum including a near-infrared region. For example, the broadband light source 11 may be a super luminescent diode (SLD). The light output from the broadband light source 11 may be transmitted to the probe 14 through the optical fiber circulator 13.

The broadband light source 11 may use a high-power laser oscillator to compensate for a degradation in sensitivity while a fast parallel optical coherence tomographic image generating method is performed.

The optical fiber circulator 13 may handle inputs and outputs of a plurality of optical fiber cables, and disperse input light or determine a direction and a proportion of light to be output. For example, the optical fiber circulator 13 may be connected to the broadband light source 11, the spectrometer 15, and the probe 14 through the optical fiber cables.

The optical fiber circulator 13 may transmit the light output from the broadband light source 11 to the probe 14, and transmit interference light output from the probe 14 to the spectrometer 15. Accordingly, a common optical path may be formed between the optical fiber circulator 13 and the probe 14.

The probe 14 may receive the light output from the broadband light source 11, radiate the light on the sample 6, generate the interference light from a measurement light reflected from the sample 6 using the Michelson interferometer, and transmit the interference light to the spectrometer 15 through the optical fiber circulator 13.

The probe 14 may include a scanning lens 141, an object lens 142, and an interferer 143.

The scanning lens 141 may disperse or diffract the light received from the broadband light source 11 into regions of a plurality of wavelengths, and radiate the dispersed light toward the sample 6.

The scanning lens 141 may include a first collimator 1411, a first dispersive element 1412, a first relay lens 1413, and a beam scanner 1414.

The first collimator 1411 may be positioned at a first ordinal position on a path of light output from a cable connected to the probe 14. The first collimator 1411 may convert the light incident from the cable into parallel lights and transmit the parallel lights to the first dispersive element 1412.

The first dispersive element 1412 may be positioned more downstream than the first collimator 1411, based on a moving direction of the light. The first dispersive element 1412 may diffract and disperse the lights incident from the first collimator 1411, and the lights output from the first dispersive element 1412 may be transmitted to the first relay lens 1413. For example, a transmission grating, a reflection grating, or a prism may be used as the first dispersive element 1412. Unless otherwise described, the description of the first dispersive element 1412 may also apply to a second dispersive element 152.

The lights incident to the first dispersive element 1412 may be dispersed sequentially by wavelength.

The first relay lens 1413 may be positioned more downstream than the first dispersive element 1412, based on a moving direction of the light entering the probe 14. The first relay lens 1413 may include a plurality of lenses, and extend an image of incident lights and transmit the received lights to the beam scanner 1414.

The beam scanner 1414 may be positioned more downstream than the first relay lens 1413, based on the moving direction of the light entering the probe 14. The beam scanner 1414 may reflect the lights incident from the first relay lens 1413 toward the sample 6 by changing an angle of incidence of the lights. For example, a galvanometer scanner or an acousto-optic deflector may be used as the beam scanner 1414. The beam scanner 1414 may include a galvanometer and a mirror connected to the galvanometer.

The object lens 142 may be positioned more downstream than the beam scanner 1414, based on the moving direction of the light entering the probe 14. The object lens 142 may refract the lights reflected from the beam scanner 1414 toward a focus of the object lens 142.

A cover glass C may be positioned between the object lens 142 and the sample 6. For example, the focus of the object lens 142 may be behind the cover glass C based on a moving direction of the radiated light.

The interferer 143 may split the light radiated to the probe 14, radiate the split light on a reference mirror 1435 and the sample 6, and form the interference light using the Michelson interferometer which synthesizes reference light reflected from the reference mirror 1435 and the measurement light reflected from the sample 6. For example, as shown in FIG. 2A, the interferer 143 may be positioned between the object lens 142 and the cover glass C. In this example, the light may move along a common path from an entrance side of the probe 14 to the object lens 142.

The interferer 143 may include a split window 1431, the reference mirror 1435, a first compensation window 1433, and a second compensation window 1434.

The split window 1431 may be positioned between the object lens 142 and the sample 6. The split window 1431 may radiate a portion of each light incident from the object lens 142 toward the sample 6 and reflect a remaining portion thereof toward the reference mirror 1435.

The split window 1431 may be disposed slantingly to reflect each light incident from the object lens 142 toward the reference mirror 1435. For example, a beam splitter 1436 may be formed on a surface of the split window 1431 to which light is incident from the object lens 142.

The beam splitter 1436 may pass a portion of light and reflect a remaining portion thereof toward the reference mirror 1435. For example, the beam splitter 1436 may form a radiated light by transmitting about 90% of the light incident from the object lens 142 toward the sample 6 and reflect the remaining about 10% of the light toward the reference mirror 1435.

The reference mirror 1435 may reflect the light reflected from the beam splitter 1436 in an opposite direction. For example, a distance between the split window 1431 and the reference mirror 1435 may be equal to a distance between the split window 1431 and the sample 6.

By the reference mirror 1435, the light radiated on the sample 6 and reflected from the sample 6, hereinafter, the measurement light, and the light reflected from the reference mirror 1435, hereinafter, the reference light, may be combined again at the split window 1431, whereby the interference light may be formed.

The first compensation window 1433 may compensate for a difference in optical path formed with respect to the reference light due to a medium of the split window 1431 while the measurement light passing through the beam splitter 1436 passes through the split window 1431.

The first compensation window 1433 and the split window 1431 may be formed of the same material. For example, the first compensation window 1433 may have a greater thickness than the split window 1431. The thickness of the first compensation window 1433 may be equal to a linear distance the radiated light passes the slantingly formed split window 1431.

The second compensation window 1434 may be disposed between the first compensation window 1433 and the reference mirror 1435. The second compensation window 1434 may compensate for a difference in optical path formed with respect to the reference light due to a medium of the cover glass C while the radiated light passes through the cover glass C. For example, the second compensation window 1434 and the cover glass C may have the same thickness.

The spectrometer 15 may receive the interference light output in response to the sample 6 being captured through the probe 14, detect a spectrum of the interference light, and acquire an interference spectral image through an analysis of the spectrum.

The spectrometer 15 may include a second collimator 151, the second dispersive element 152, a second relay lens 153, and a line camera 154.

The second collimator 151 may convert the interference light incident to the spectrometer 15 into parallel lights.

The second dispersive element 152 may disperse the interference lights incident from the second collimator 151 by wavelength. For example, the second dispersive element 152 may disperse the interference lights based on a unit of wavelength the same as that of the first dispersive element 1412. That is, a range of wavelength for each region into which the light is dispersed by the second dispersive element 152 may be the same as a range of wavelength for each of the regions $\Delta\lambda_1$ to $\Delta\lambda_N$ into which the light is dispersed by the first dispersive element 1412. Of course, as described with respect to the first dispersive element 1412, it may be understood by those skilled in the art that ranges of wavelengths of a plurality of regions into which the light is dispersed by the second dispersive element 152 may differ from each other. For example, a transmission grating, a reflection grating, or a prism may be used as the second dispersive element 152.

The second relay lens 153 may extend an image of the interference lights dispersed at the second dispersive element 152 and transmit the interference lights to the line camera 154.

The line camera 154 may receive the dispersed interference lights and form the interference spectral image. For example, the dispersed lights incident to the line camera 154 may be divided into N regions by wavelength, N being an integer greater than or equal to "2", and the N regions of the dispersed interference lights may be incident on respective pixels of the line camera 154.

The line camera 154 may include an image sensor including at least N pixels. For example, the at least N pixels may be arranged in a line, and each of the N regions of the dispersed interference lights may be input into one pixel of the line camera 154.

The controller 16 may generate a tomographic image of the sample 6 by measuring depth information of the sample 6 through a Fourier transformation of the interference spectral image received from the line camera 154.

The controller 16 may control the beam scanner 1414 to change a position at which the radiated light is radiated on the sample 6. For example, the controller 16 may discretely control the beam scanner 1414 such that the radiated light may be incident at a position changed by a preset distance G on an image region.

Figure 2B:
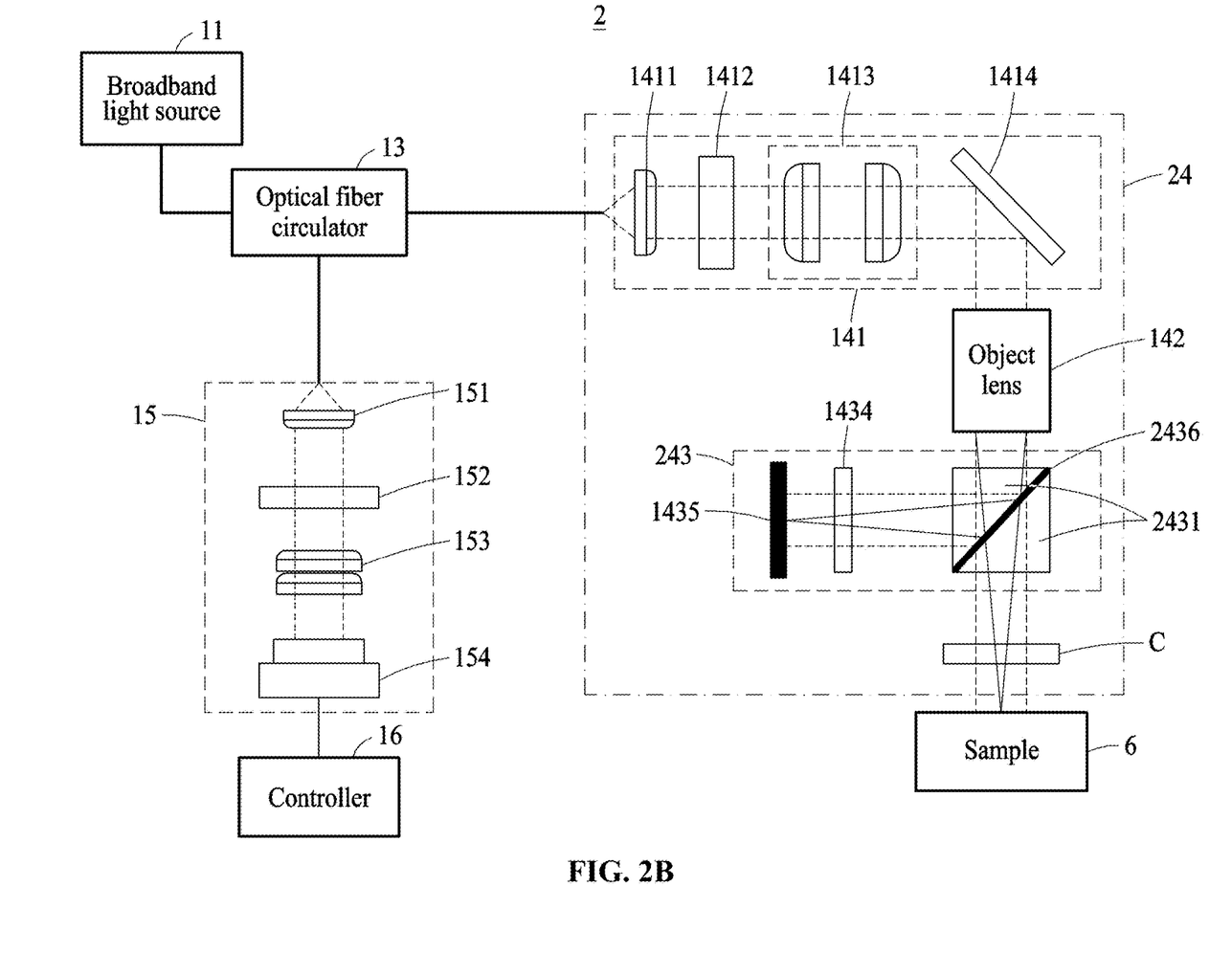
FIG. 2B is a block diagram illustrating a fast parallel optical coherence tomographic image generating apparatus according to an example embodiment.

FIG. 2B is a block diagram illustrating a fast parallel optical coherence tomographic image generating apparatus according to an example embodiment.

Referring to FIG. 2B, a fast parallel optical coherence tomographic image generating apparatus 2 may include the broadband light source 11, the optical fiber circulator 13, the probe 14, the spectrometer 15, and the controller 16.

The probe 24 may include the scanning lens 141, the object lens 142, an interferer 243, and the cover glass C.

For example, the interferer 243 may include a cube-type split window 2431, the reference mirror 1435, and the compensation window 1434.

The cube-type split window 2431 may include a beam splitter 2436 disposed slantingly to reflect lights incident from the object lens 142 toward the reference mirror 1435. The cube-type split window 2431 may have a symmetrical shape with respect to the beam splitter 2436. By the above shape, unlike the example of FIG. 2A, the difference in optical path caused by the medium of the split window 1431 of FIG. 2A positioned on only one side of the beam splitter 1436 of FIG. 2A may not need to be compensated for, and thus the fast parallel optical coherence tomographic image generating apparatus 2 may be configured more simply.

Figure 2C:
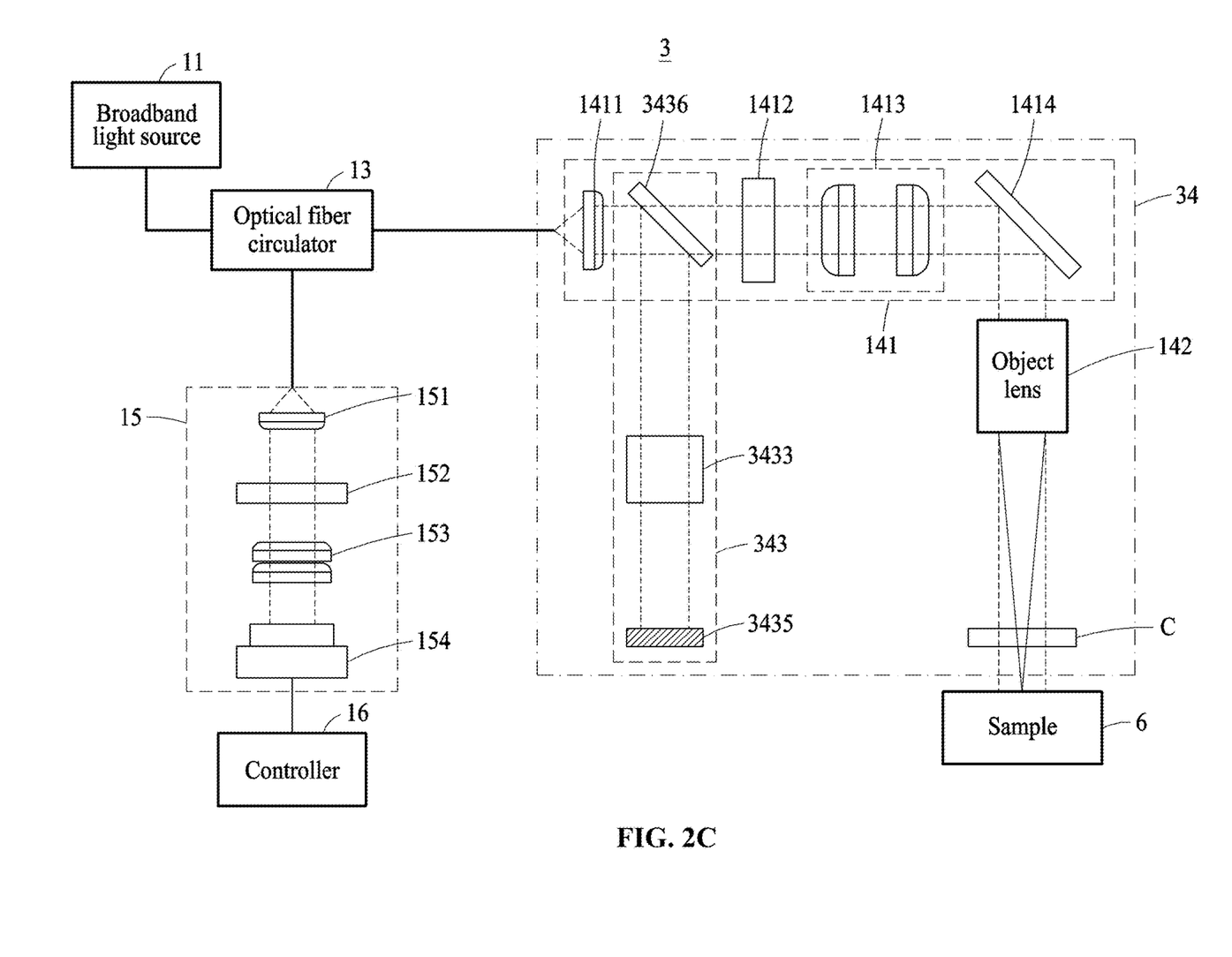
FIG. 2C is a block diagram illustrating a fast parallel optical coherence tomographic image generating apparatus according to an example embodiment.

FIG. 2C is a block diagram illustrating a fast parallel optical coherence tomographic image generating apparatus according to an example embodiment.

Referring to FIG. 2C, a fast parallel optical coherence tomographic image generating apparatus 3 may include the broadband light source 11, the optical fiber circulator 13, a probe 34, the spectrometer 15, and the controller 16.

The probe 34 may include the scanning lens 141, the object lens 142, an interferer 343, and the cover glass C.

For example, the interferer 343 may include a beam splitter 3436, a compensator 3433, and a reference mirror 3435.

The beam splitter 3436 may be disposed between the first collimator 1411 and the first dispersive element 1412. The beam splitter 3436 may form a radiated light by transmitting a portion of light incident from the first collimator 1411 toward the sample 6 through the first dispersive element 1412, and reflect a remaining portion of the light toward the reference mirror 3435 not through the first dispersive element 1412.

The compensator 3433 may be disposed between the beam splitter 3436 and the reference mirror 3435. The compensator 3433 may compensate for a difference between an optical path of measurement light moving from the beam splitter 3436 to the sample 6 and an optical path of reference light moving from the beam splitter 3436 to the reference mirror 3435. For example, at least one optical system or a frequency-domain optical delay line (FDODL) may be used as the compensator 3433. Meanwhile, the compensator 3433 may replace the compensation window 1433, 1434 described in the former example embodiments.

Figure 3:
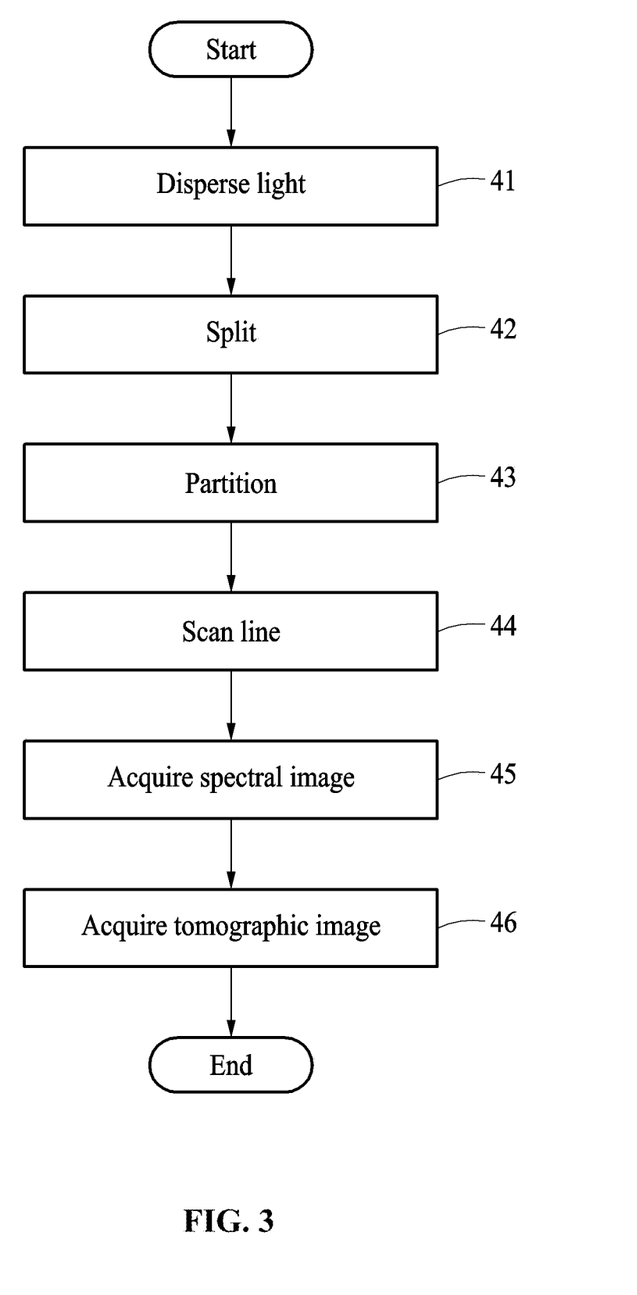
FIG. 3 is a flowchart illustrating a fast parallel optical coherence tomographic image generating method according to an example embodiment.
Figure 4:
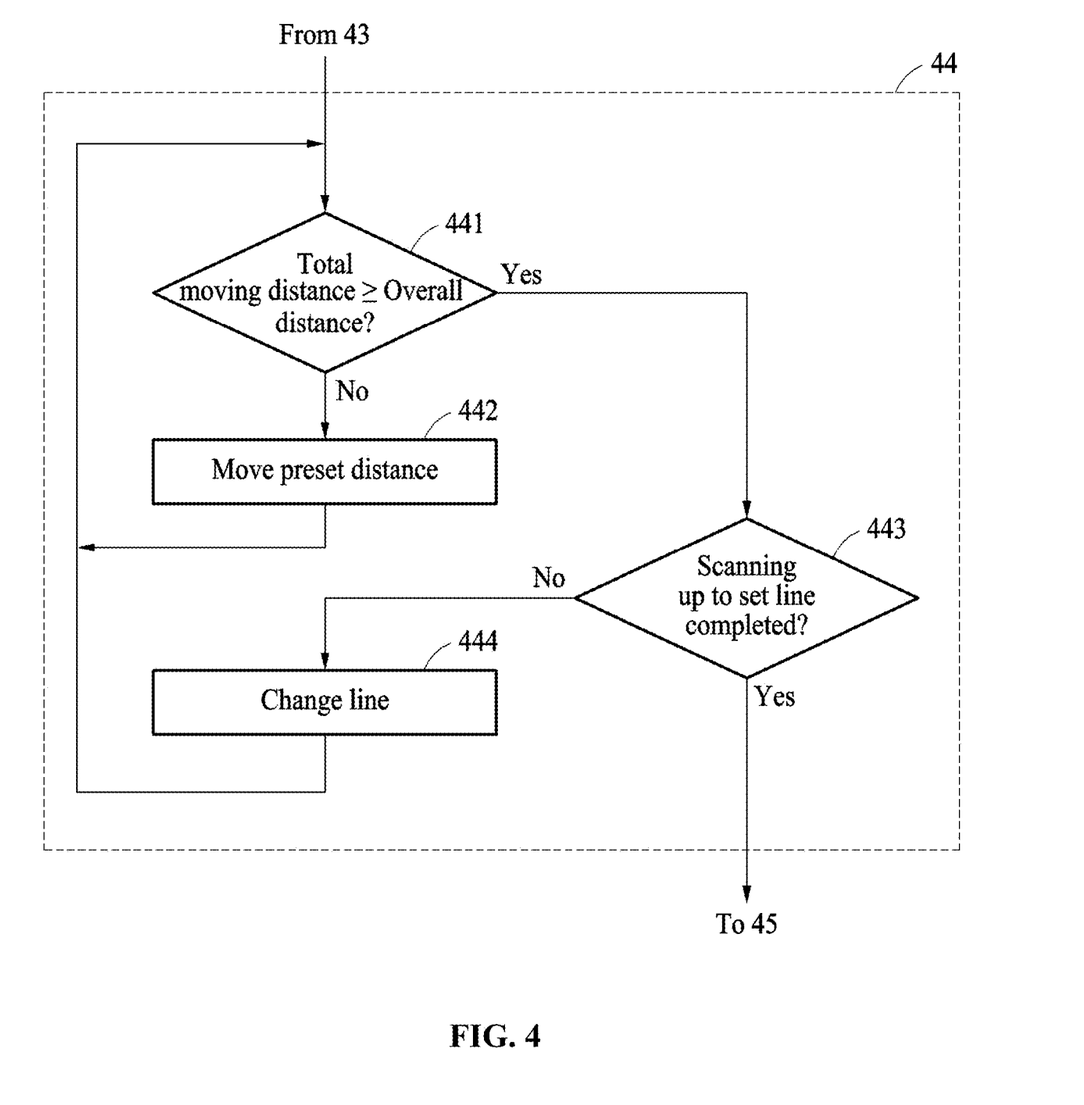
FIG. 4 is a flowchart illustrating an operation of line scanning according to an example embodiment.
Figure 5:
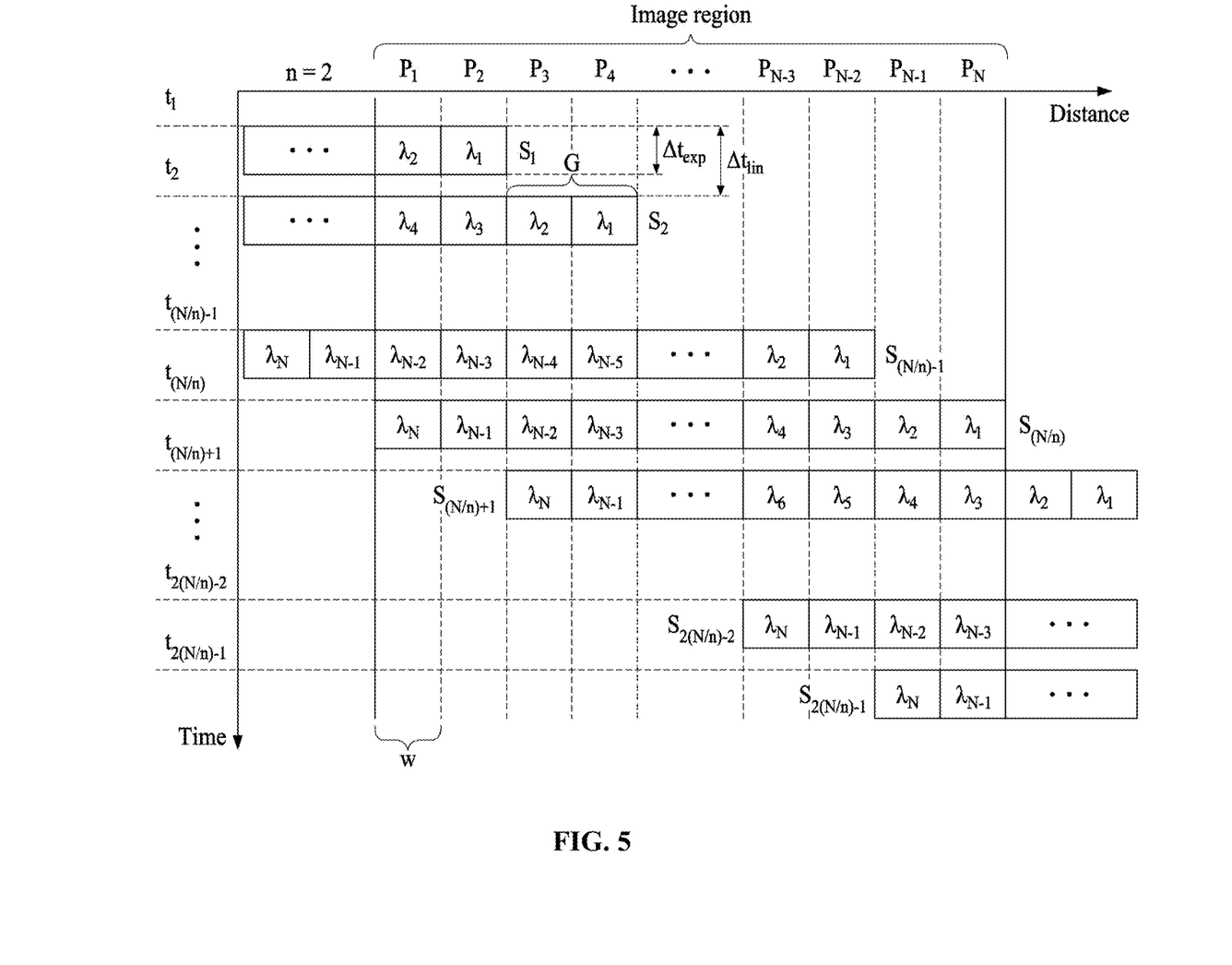
FIG. 5 illustrates a process of scanning a parallel optical coherence tomographic image according to an example embodiment.

FIG. 3 is a flowchart illustrating a fast parallel optical coherence tomographic image generating method according to an example embodiment, FIG. 4 is a flowchart illustrating an operation of line scanning according to an example embodiment, and FIG. 5 illustrates a process of scanning a parallel optical coherence tomographic image according to an example embodiment. In detail, FIG. 5 illustrates a process of completing scanning of a single line by radiating light while changing a position of radiation over time on the single line of an image region of the sample 6.

Referring to FIGS. 3 through 5, the fast parallel optical coherence tomographic image generating method may include operation 41 of dispersing light, operation 42 of splitting, operation 43 of partitioning, operation 44 of scanning a line, operation 45 of acquiring a spectral image, and operation 46 of acquiring a tomographic image. An order shown in the flowchart of FIG. 3 is only an example. Unless otherwise described, the order of operations is not limited thereto, and the operations may be performed concurrently. Further, the description will be provided based on the example of FIG. 2A and may also similarly apply to the examples of FIGS. 2B and 2C.

In operation 41, a light input from the broadband light source 11 into the probe 14 may be dispersed by wavelength as passing through the first dispersive element 1412. In operation 41, the light input into the probe 14 may be dispersed by the first dispersive element 1412 into N spectral regions $\Delta\lambda_1$ through $\Delta\lambda_N$ sequentially from a low wavelength to a high wavelength. As shown in FIG. 5, light corresponding to the spectral regions may be radiated on the sample 6 at the same physical width. The width may also be referred to as a "spectral distance w". Meanwhile, it may be understood by those skilled in the art that despite the same spectral distance w, ranges $\Delta\lambda$ of wavelengths of spectral regions $\Delta\lambda_1$ through $\Delta\lambda_N$ may differ from each other depending on a design specification of the first dispersive element 1412.

In operation 42, the light input into the probe 14 may be split into radiated light to be radiated on the sample 6 and reference light to be reflected toward the reference mirror 1435, as passing through the split window 1431. In the examples of FIGS. 2A and 2B, operation 42 may be performed after operation 41 is performed. However, in the example of FIG. 2C, operation 42 may be performed before operation 41 is performed.

As shown in FIG. 5, in an example in which a section on the sample 6 from which a parallel optical coherence tomographic image is to be acquired is referred to as an "image region", in operation 43, the controller 16 may partition the image region into N regions $P_1$ through $P_N$ in one direction. In this example, a physical width of each image region may be equal to the spectral distance w.

In operation 44, the controller 16 may radiate the radiated light on each line of the sample 6 to be measured while controlling the beam scanner 1414 to move the dispersed radiated light.

In operation 44, the radiated light dispersed by wavelength along a series of lines may be radiated while being moved in a direction from one side to another side in the image region, that is, in a longitudinal direction of a line formed by the dispersed radiated light.

In operation 44, before each line is scanned, the controller 16 may control the beam scanner 1414 to place the radiated light in an initial state of each line.

As shown in FIG. 5, a spectral region $\Delta\lambda_1$ having a shortest wavelength, among N spectral regions into which the radiated light is dispersed, may be positioned in a rightmost image region in the initial state. In this example, a single line of the sample 6 may be scanned as a right spectral region of the radiated light moves along the single line of the image region in a rightward direction from a leftmost image region $P_1$ to a rightmost image region $P_N$ on the sample 6.

In an example in which the dispersed radiated light moves along the line of the image region, the controller 16 may discretely control the beam scanner 1414 such that the radiated light may be incident on the image region at a position changed by the "preset distance G".

Here, the preset distance G may be a distance corresponding to a number n of image regions to be skipped by an end portion of the radiated light among the N image regions. That is, the preset distance G may be expressed by a product of the spectral distance w or the width of the image region and the number n of the image regions to be skipped.

In an example in which the number n of the image regions to be skipped by the radiated light is set to "2" as shown in FIG. 5, the controller 16 may discretely control the beam scanner 1414 to move the radiated light two spectral distances w or two widths of the image region at a time.

In this example, a total distance the radiated light is moved on the sample 6 to scan all single lines of the image region may be referred to as an "overall distance D". The overall distance D may be a total distance the radiated light is moved from an initial state in which the rightmost spectral region of the radiated light is positioned on a leftmost image region to an end state in which a leftmost spectral region of the radiated light is positioned on a rightmost image region, and the overall distance D may be obtained as expressed by Equation 1.

$$D = 2(N \times x) - 2(n \times w) \quad \text{[Equation 1]}$$

(Here, D: the overall distance, N: the number of the image regions, n: the number of the image regions to be skipped by the radiated light, and w: spectral distance.)

In an example in which the radiated light completes scanning of a single line by moving the overall distance D on the sample 6 as described above, the radiated light may move to a subsequent line immediately adjacent to the scanned line and iteratively perform the operation described above. For example, in operation 44, line scanning may be iteratively performed a number of times corresponding to a preset number of "set lines".

Operation 44 may include operation 441 of verifying a line, operation 442 of moving a preset distance, operation 443 of verifying set lines, and operation 444 of changing a line.

In operation 441, the beam scanner 1414 may verify whether a distance the radiated light is moved by the beam scanner 1414 is greater than or equal to the overall distance D. That is, whether scanning of a single line on the image region is completed may be verified.

In response to determination that the distance the radiated light is moved is greater than or equal to the overall distance D, operation 443 may be performed.

If the distance the radiated light is moved is less than the overall distance D, operation 442 may be performed. In operation 442, the controller 16 may control the beam scanner 1414 to move the radiated light the preset distance G corresponding to the preset number n of image regions to be skipped.

After operation 442 is performed, operation 441 may perform again such that the above process may be iteratively performed until scanning of all single lines on the image region is completed.

A number of times T operation 442 is performed in a process of scanning a single line may be expressed by Equation 2.

$$T = 2\left(\frac{N}{n}\right) - 1 \quad \text{[Equation 2]}$$

(Here, T: Number of times operation of moving the preset distance is performed, N: Number of image regions, and n: Number of image regions to be skipped.)

In an example in which the number n of the image regions to be skipped is "2" as shown in FIG. 5, two spectral regions of the radiated light may be respectively positioned in first two image regions $P_1$ and $P_2$ in the initial state. That is, the spectral region $\Delta\lambda_1$ of the radiated light having a shortest wavelength may be positioned in the image region $P_2$, and the spectral region $\Delta\lambda_2$ of the radiated light having a subsequently shortest wavelength may be positioned in the image region $P_1$.

Then, operation 442 may be iteratively performed such that the radiated light may be moved by skipping image regions corresponding to the preset distance G, that is, the number n of image regions to be skipped.

In an example in which the radiated light moves the overall distance D and scans all the single lines of the image region, all the image regions may be exposed throughout all wavelengths of the radiated light although the number of spectral regions of the radiated light being exposed may decrease in proportion to the number n of image regions to be skipped.

By the above structure, the number n of image regions to be skipped may be set to be relatively great, the preset distance G the radiated light is to be moved while scanning a single line on the image region may increase. That is, a number of times operation 442 is performed may decrease, whereby a time for scanning a single line may be reduced, and thus a time for generating the parallel optical coherence tomographic image of the sample 6 may be reduced.

If the distance the radiated light is moved is greater than or equal to the overall distance D, operation 443 may be performed. In operation 443, whether scanning of all the image regions is completed may be verified.

In detail, in operation 443, whether a number of lines scanned thus far is equal to the preset number of set lines may be verified.

In response to determination that the scanning is completed in operation 443, operation 44 may be terminated.

If the number of the scanned lines is less than the preset number of set lines, operation 444 may be performed. For example, in operation 444, the controller 16 may control the beam scanner 1414 to move the radiated light to be positioned in an initial state of a subsequent line adjacent to the scanned line of the image region.

When operation 444 is completed, operation 441 may be performed again to perform scanning on a new line.

In operation 45, interference light formed in response to interference of measurement light radiated on the sample 6 and reflected from the sample 6 and reference light reflected from the reference mirror 1435 in operation 44 may be input into the spectrometer 15.

In operation 45, the second collimator 151 may disperse the interference light into N regions by wavelength and input the N regions into respective pixels of the line camera 154, thereby forming an interference spectral image.

In operation 46, the controller 16 may generate a tomographic image of the sample 6 through the interference spectral image formed by the spectrometer 15.

Figure 6A:
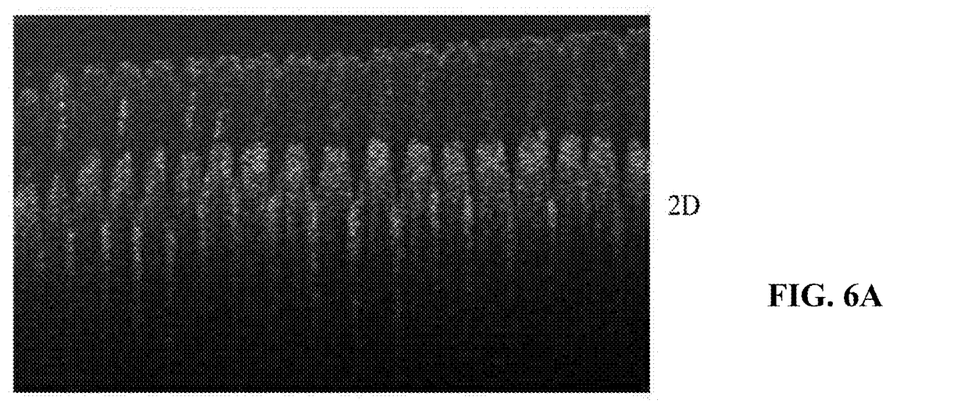
FIGS. 6A and 6B illustrate tomographic images of a finger acquired using a fast parallel optical coherence tomographic image generating apparatus according to an example embodiment.
Figure 6B:
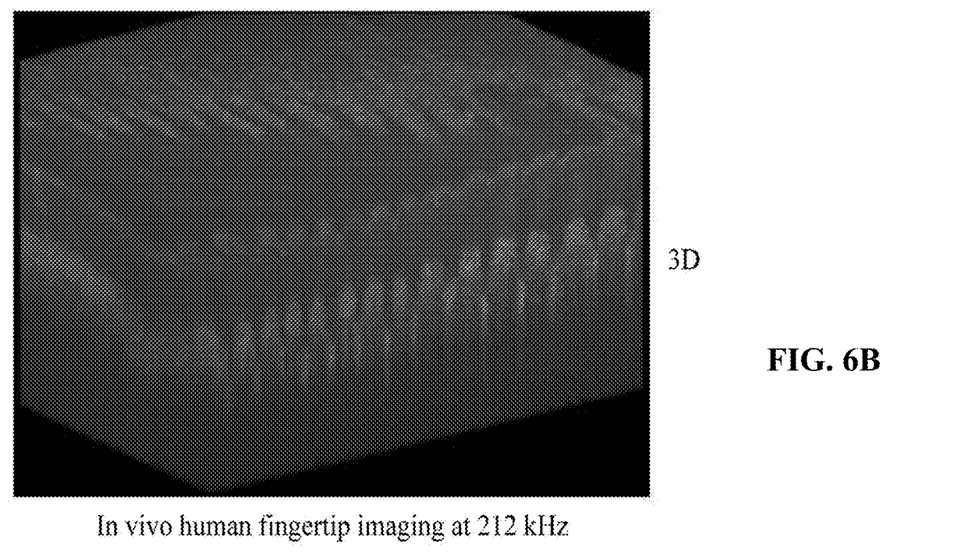
Figure 7A:
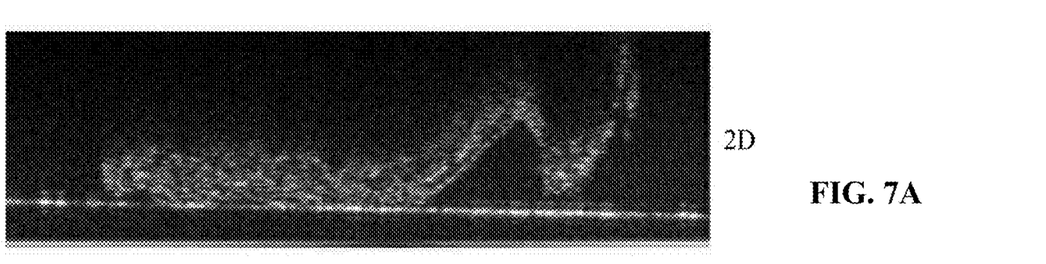
FIGS. 7A and 7B illustrate tomographic images of a leaf acquired using a fast parallel optical coherence tomographic image generating apparatus according to an example embodiment.
Figure 7B:
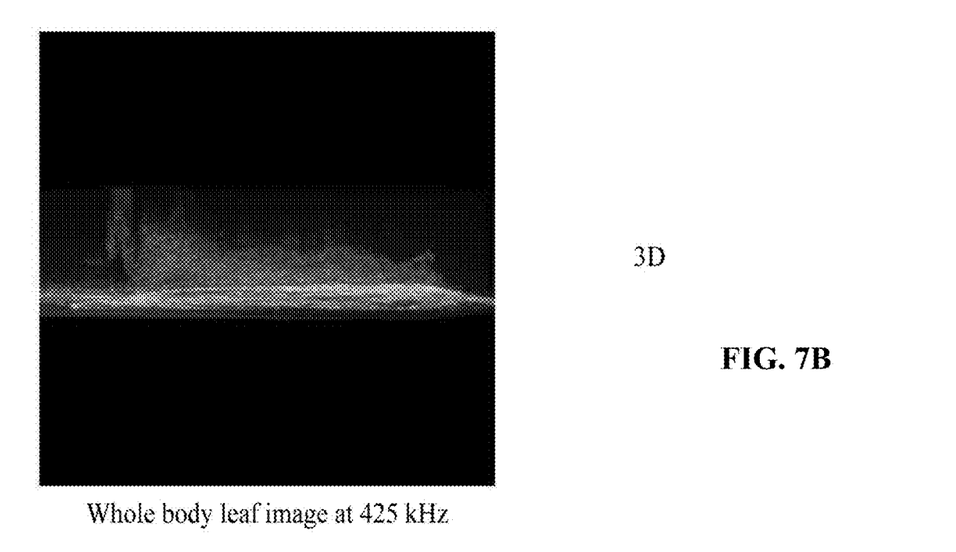

FIGS. 6A and 6B illustrate tomographic images of a finger acquired using a fast parallel optical coherence tomographic image generating apparatus according to an example embodiment, and FIGS. 7A and 7B illustrate tomographic images of a leaf acquired using a fast parallel optical coherence tomographic image generating apparatus according to an example embodiment.

Images of FIGS. 6A and 6B are tomographic images acquired by capturing a fingertip of a person through the fast parallel optical coherence tomographic image generating apparatus 1 by setting a sampling interval, for example, a width w of each image region, to "5" micrometers (µm) and setting the number n of image regions to be skipped by the radiated light to "4". In this example, the sample 6 may be scanned at a speed of about 250 k axial scans per second (A-scan/s), and the tomographic images may be measured at a depth of about 1.1 millimeters (mm).

Referring to FIGS. 6A and 6B, it may be learned that the stratum corneum of the fingertip is clearly visible, along with the border of the epidermis and dermal junction. As described above, by the optical coherence tomographic image generating method, although the number n of image regions to be skipped by the radiated light on the sample 6 increases, that is, although the sampling number by wavelength of the radiated light decreases, clear tomographic images may be acquired.

Images of FIGS. 7A and 7B are tomographic images acquired by capturing a stemmed leaf through the fast parallel optical coherence tomographic image generating apparatus 1 by setting a sampling interval to "5" µm and setting the number n of image regions to be skipped by the radiated light to "8". In this example, the sample may be scanned at a speed of about 500 k A-scan/s, and the tomographic images may be measured at a depth of about 0.55 mm.

Referring to FIGS. 7A and 7B, it may be learned that there appear distinctive boundaries between palisade parenchyma and spongy parenchyma of the stemmed leaf. As described above, by the fast parallel optical coherence tomographic image generating method, although the number n of image regions to be skipped by the radiated light on the sample 6 increases, that is, although the sampling number by wavelength of the radiated light decreases, clear tomographic images may be acquired.

By the fast parallel optical coherence tomographic image generating method using the fast parallel optical coherence tomographic image generating apparatus 1, the speed of scanning the sample 6 may increase as the number n of image regions to be skipped by the radiated light on the sample 6 increases. Considering a general spectrally encoded OCT device has an imaging speed of about 312 k A-scan/s, the fast parallel optical coherence tomographic image generating apparatus 1 may perform imaging at a speed of about 500 k A-scan/s, which is improved about 160% when compared to the imaging speed of the general OCT device.

In this example, although the sampling number decreases, the resolution, that is, the optical wavelength resolution, may not decrease, whereas the sensitivity and the measurement depth of the system may decrease. However, the decrease in the sensitivity may be compensated for by increasing an output of the broadband light source 11, and the decrease in the measurement depth may not be considerable, and thus it may be possible to generate a tomographic image fast while preventing a deterioration in a quality of the tomographic image to be generated.

According to example embodiments, a fast parallel optical coherence tomographic image generating method may generate a tomographic image of a sample fast.

According to example embodiments, a fast parallel optical coherence tomographic image generating apparatus may image a sample fast without causing a decrease in resolution and sensitivity.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A fast parallel optical coherence tomographic image generating method comprising:
dispersing light into N spectral regions $\Delta\lambda_1$ through $\Delta\lambda_N$ sequentially from a low frequency wavelength to a high frequency wavelength, the light being emitted from a broadband light source of a fast parallel optical coherence tomographic image generating apparatus, N being an integer greater than or equal to 2;
splitting the light emitted from the broadband light source to be incident on a sample and a reference mirror;
partitioning the sample into N image regions $P_1$ through $P_N$;
discretely controlling a beam scanner such that the light emitted from the broadband light source is incident on the sample at a position changed by a preset distance;
acquiring an interference spectral image through interference light formed in response to interference of measurement light and reference light, the measurement light being light corresponding to at least two of the N spectral regions and being reflected from the sample and the reference light being light corresponding to the at least two spectral regions and being reflected from the reference mirror; and
generating a tomographic image of the sample using the interference spectral image,
wherein the N spectral regions are incident on the sample at the same spectral distance which is a physical width, and a distance between the N image regions of the sample is equal to the spectral distance,
wherein the preset distance is expressed by a product of the spectral distance and a number of image regions to be skipped by an end portion of the light radiated on the sample for each step among the N image regions,
wherein in the discretely controlling, an overall distance the light is to be moved by the beam scanner along a single line is calculated according to:

$$D=2(N\times x)-2(n\times w), \text{ and}$$

wherein, D is the overall distance, N is a number of the image regions, n is the number of image regions to be skipped by the end portion of the light radiated on the sample for each step, and w is the spectral distance.

2. The fast parallel optical coherence tomographic image generating method of claim 1, wherein the discretely controlling comprises:
determining whether a distance the radiated light is moved by the beam scanner is greater than the overall distance;
moving the radiated light to an initial position of a subsequent line, if the distance the radiated light is moved is greater than the overall distance; and
moving the radiated light the preset distance, if the distance the radiated light is moved is less than the overall distance.

3. The fast parallel optical coherence tomographic image generating method of claim 1, wherein the generating comprises dividing the interference spectral image into N regions by wavelength and inputting the N regions into respective pixels of a line scan camera.

4. The fast parallel optical coherence tomographic image generating method of claim 3, wherein a number of the pixels of the line scan camera is greater than or equal to N, and
the N regions into which the interference spectral image is divided are incident on the respective pixels of the line scan camera.

5. The fast parallel optical coherence tomographic image generating method of claim 1, wherein the fast parallel optical coherence tomographic image generating apparatus comprises an object lens configured to receive light reflected from the beam scanner, and has a common optical path from the broadband light source to the object lens.

6. The fast parallel optical coherence tomographic image generating method of claim 5, wherein the fast parallel optical coherence tomographic image generating apparatus further comprises:
a split window disposed between the object lens and the sample, the split window including a beam splitter configured to reflect light incident from the object lens toward the reference mirror.

7. The fast parallel optical coherence tomographic image generating method of claim 6, wherein the fast parallel optical coherence tomographic image generating apparatus further comprises:
a first compensation window disposed between the split window and the reference mirror, the first compensation window having a greater thickness than the split window so as to compensate for a difference in optical path of the reference light.

8. The fast parallel optical coherence tomographic image generating method of claim 7, wherein the fast parallel optical coherence tomographic image generating apparatus further comprises:
   a cover glass positioned between the split window and the sample; and
   a second compensation window disposed between the first compensation window and the reference mirror, the second compensation window and the cover glass having the same thickness so as to compensate for a difference in optical path of the reference light.

9. The fast parallel optical coherence tomographic image generating method of claim 5, wherein the fast parallel optical coherence tomographic image generating apparatus further comprises:
   a cube-type split window disposed between the object lens and the sample, the cube-type split window including a beam splitter configured to reflect light incident from the object lens toward the reference mirror, the cube-type split window having a symmetrical shape with respect to the beam splitter.

* * * * *